(12) United States Patent
Beute et al.

(10) Patent No.: US 10,653,347 B2
(45) Date of Patent: May 19, 2020

(54) NON-INVASIVE MEASUREMENT DEVICE AND METHOD FOR ESTIMATING LOCAL METABOLIC PARAMETERS

(71) Applicant: APD ADVANCED PERFUSION DIAGNOSTICS, Lyons (FR)

(72) Inventors: Jan Beute, Almere (NL); Remi Bonidal, Lyons (FR)

(73) Assignee: APD ADVANCED PERFUSION DIAGNOSTICS, Lyons (FR)

( * ) Notice: Subject to any disclaimer, the term of this patent is extended or adjusted under 35 U.S.C. 154(b) by 698 days.

(21) Appl. No.: 15/025,663

(22) PCT Filed: Sep. 26, 2014

(86) PCT No.: PCT/EP2014/070605
§ 371 (c)(1),
(2) Date: Mar. 29, 2016

(87) PCT Pub. No.: WO2015/044336
PCT Pub. Date: Apr. 2, 2015

(65) Prior Publication Data
US 2016/0213293 A1     Jul. 28, 2016

(30) Foreign Application Priority Data
Sep. 30, 2013  (FR) ..................... 13 59442

(51) Int. Cl.
*A61B 5/1455* (2006.01)
*A61B 5/1495* (2006.01)
(Continued)

(52) U.S. Cl.
CPC ........ *A61B 5/14552* (2013.01); *A61B 5/0075* (2013.01); *A61B 5/1455* (2013.01);
(Continued)

(58) Field of Classification Search
CPC . A61B 5/0075; A61B 5/14546; A61B 5/1495; A61B 5/1455; G01N 33/721; G01N 33/726
(Continued)

(56) References Cited

U.S. PATENT DOCUMENTS 5,413,100 A * 5/1995 Barthelemy ....... A61B 5/14551
600/326
6,104,938 A * 8/2000 Huiku .................. A61B 5/0059
600/322
(Continued)

OTHER PUBLICATIONS

Mendelson, "Pulse Oximetry", Wiley Encyclopedia of Biomedical Engineering, p. 1-18, 2006.*
(Continued)

*Primary Examiner* — Eric F Winakur
(74) *Attorney, Agent, or Firm* — Craft Chu PLLC; Andrew W. Chu

(57) ABSTRACT

A method for estimating a local metabolic parameter of an area of tissue of a patient. The method receives light intensities from the area of tissue in question for at least three different wavelengths selected according to the absorptive power of different types of haemoglobin, on the basis of the absorbancy values calculated using the light intensities measured for the three wavelengths. The method determines a oxyhaemoglobin concentration and a deoxyhaemoglobin concentration and estimates at least one local metabolic parameter on the basis of the calculated oxyhaemoglobin and deoxyhaemo-globin concentrations.

15 Claims, 5 Drawing Sheets

Figure 1:
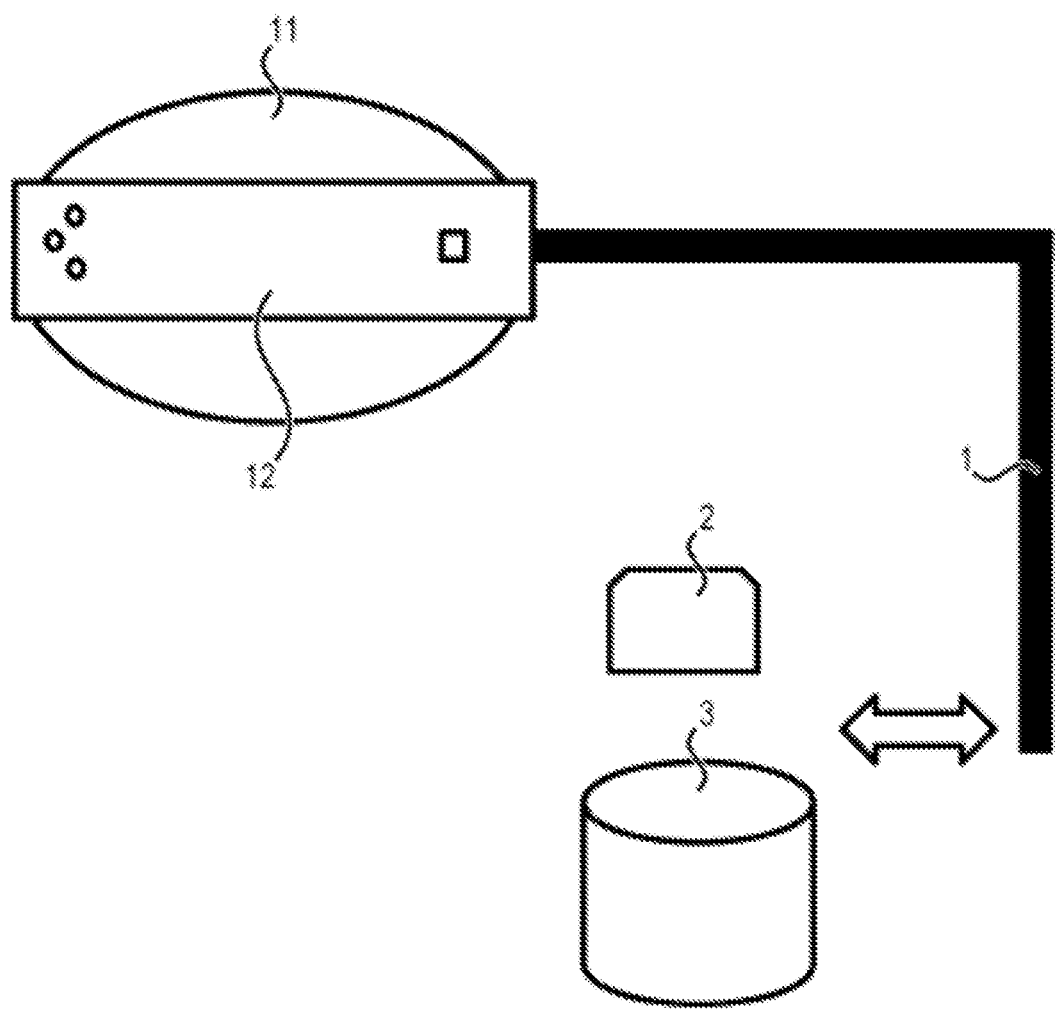

(51) Int. Cl.
*A61B 5/00* (2006.01)
*G01N 33/72* (2006.01)
*A61B 5/145* (2006.01)

(52) U.S. Cl.
CPC ........ *A61B 5/1495* (2013.01); *A61B 5/14546* (2013.01); *A61B 5/14551* (2013.01); *G01N 33/721* (2013.01); *G01N 33/726* (2013.01)

(58) Field of Classification Search
USPC ................................................. 600/300–399
See application file for complete search history.

(56) References Cited

U.S. PATENT DOCUMENTS

| | | | |
|---|---|---|---|
| 6,134,460 A * | 10/2000 | Chance | A61B 5/14551 600/310 |
| 6,334,065 B1 * | 12/2001 | Al-Ali | A61B 5/14551 600/323 |
| 6,456,862 B2 * | 9/2002 | Benni | A61B 5/14553 600/331 |
| 6,859,658 B1 * | 2/2005 | Krug | A61B 5/14552 600/323 |
| 7,738,935 B1 | 6/2010 | Turcott | |
| 2001/0047128 A1 | 11/2001 | Benni | |
| 2003/0176776 A1 * | 9/2003 | Huiku | A61B 5/14551 600/322 |
| 2007/0282183 A1 | 12/2007 | Scholler et al. | |
| 2008/0200780 A1 | 8/2008 | Schenkman et al. | |
| 2009/0076354 A1 | 3/2009 | Huiku | |
| 2009/0281403 A1 * | 11/2009 | Benni | A61B 5/14551 600/323 |
| 2010/0331636 A1 * | 12/2010 | Hubner | A61B 5/0059 600/310 |
| 2011/0054298 A1 * | 3/2011 | Stamnes | A61B 5/0059 600/407 |
| 2012/0108925 A1 | 5/2012 | Kuhn | |
| 2013/0204102 A1 * | 8/2013 | Sen | A61B 5/14535 600/322 |
| 2015/0109617 A1 * | 4/2015 | Gilbert | A61B 5/14532 356/300 |

OTHER PUBLICATIONS

International Search Report with English Language Translation, dated Nov. 3, 2014, Application No. PCT/EP2014/070605.

* cited by examiner

NON-INVASIVE MEASUREMENT DEVICE AND METHOD FOR ESTIMATING LOCAL METABOLIC PARAMETERS

TECHNICAL FIELD

The present invention relates to the general technical field of devices and non-invasive measuring methods for estimating metabolic parameters of an organ of a patient, such as the digestive tract of a human being or an animal.

It can be used in many applications to protect patients from conditions linked to blood, especially thromboses, embolisms, haemorrhages, homeopathies and the presence of abnormal elements in the blood.

It especially provides the user with information relative to splanchnic microcirculation to assist him in the choice of treatments adapted to the patient.

GENERAL PRESENTATION OF PRIOR ART

In the medical field it is often necessary to control good tissue oxygenation of a patient.

Tissue oxygenation is assured by the blood of the patient, which delivers oxygen and nutrients to all parts of the body of the patient. Blood vessels enable circulation of the blood in the organism.

The blood circulation can be divided into two aspects: macrocirculation and microcirculation.

Macrocirculation comprises all vessels of a diameter greater than 150-300 μm, such as elastic, large-calibre, proximal arteries, and more distal arteries of average size which are muscular in nature. One of the main functions of macrocirculation relates to the transport of blood from the heart to the other organs.

Microcirculation comprises all the vessels of a diameter less than 150-300 μm, such as small arteries, arterioles, capillaries and veinlets. Microcirculation is a link between blood and cell. Tissues and cells are supplied with oxygen via this link.

Many devices and methods for estimating macrocirculatory parameters are known. These devices and methods guide the user in choice of treatment for optimising these macrocirculatory parameters.

Yet, even if the optimisation of macrocirculatory parameters is necessary, this is not sufficient to guarantee good tissue oxygenation of the patient.

In fact, in some circumstances found in intensive medicine the presence of alterations of microcirculatory flow, at the origin of cellular hypoxia, coexists with the presence of quite adequate macrocirculatory flows.

Better knowledge of physiopathological microcirculatory mechanisms associated with closer monitoring of tissue perfusion is therefore necessary to improve patient care.

Presently no device controls the physiopathological microcirculatory mechanisms of a patient in real time and minimaly invasively, in particular at microcirculatory flows.

An aim of the present invention is to propose a device and method for estimating local metabolic parameters of a patient in real time.

In the scope of the present invention "local metabolic parameters" mean metabolic parameters located near measuring points acquired to enable estimation of these parameters, this proximity extending to the scale of an organ.

PRESENTATION OF THE INVENTION

For this purpose, the invention proposes a method for estimating at least one local metabolic parameter of a tissue area of a patient, characterized in that the method comprises the following steps:

Reception of measured light intensities for the relevant tissue area, said light intensities being measured by an acquisition device for at least three different wavelengths of between 600 and 1000 nm, said wavelengths being selected as a function of the absorptivity of different types of hemoglobin, such as oxyhemoglobin and deoxyhemoglobin, the reception step consisting of receiving, for each wavelength, a plurality of measured light intensities at different instants of a period of heartbeat, Selection, for each wavelength, of measured light intensities at at least one instant of the cardiac cycle for which the aim is to estimate said at least one local metabolic parameter, Calculation, from selected light intensities, of absorbance values for the three wavelengths, Determination, from absorbance values calculated for the three wavelengths:
of a concentration of oxyhemoglobin,
of a concentration of deoxyhemoglobin,
given the tissue absorbance in the estimation of concentrations of oxyhemoglobin and deoxyhemoglobin, Estimation of at least one local metabolic parameter from concentrations of calculated oxyhemoglobin and deoxyhemoglobin.

The method according to the invention provides local characteristics of a tissue area for which the aim is to estimate local metabolic parameters. The use of a third additional wavelength enables estimation of concentrations of oxyhemoglobin and deoxyhemoglobin given the light loss due to tissue. Also, the fact of selecting measured light intensities at least at one instant of the cardiac cycle determines concentrations of oxyhemoglobin and deoxyhemoglobin for at least one category of blood from the venous blood, the arterial blood and total blood, Preferred but non-limiting aspects of the method according to the invention are the following:
the selection step consists of selecting, from all the measured light intensities, light intensities for which the amount of arterial blood is minimum in the relevant tissue area, such that the determined concentrations are representatives of concentration of oxyhemoglobin and deoxyhemoglobin in the venous blood;
Of course, the measuring frequency of absorbance values at the three wavelengths is far greater than the heartbeat frequency of the patient, which measures a plurality of light intensities during a heartbeat period,
Also, the reader will appreciate that the selection step can be automatically conducted (by means of an adapted detection algorithm) or manually from parameters informed by the practitioner, this selection depending on the local metabolic parameter(s) to be estimated,
the selection step consists of selecting, from all the measured light intensities, light intensities for which the amount of arterial blood is maximum in the relevant tissue area, such that the determined concentrations are representative of concentration of oxyhemoglobin and deoxyhemoglobin in the total blood;
the estimation step comprises estimation of oxygen consumption in the relevant tissue area from concentrations of oxyhemoglobin and deoxyhemoglobin in the total blood and in the venous blood;
the method further comprises a step, for each of the three wavelengths, for obtaining denoised values corresponding to the results of a mathematical function applied to a plurality of absorbance values, the determination step consisting of calculating the concentrations of oxyhemoglobin and deoxyhemoglobin from denoised values;

This improves the quality of estimation of the local metabolic parameter(s), the reception step comprises reception of measured light intensities for:

- a first wavelength at which the light absorption of the deoxyhemoglobin is greater than the light absorption of the oxyhemoglobin, such as a first wavelength comprised between 600 and 700 nm, and preferably equal to 660 nm,
- a second wavelength (906 nm) at which the light absorption of the oxyhemoglobin is greater than the light absorption of the deoxyhemoglobin, such as a second wavelength comprised between 900 and 1000 nm, preferably equal to 906 nm, and
- a third wavelength (810 nm) corresponding to an isobestic point at which light absorptions of oxyhemoglobin and deoxyhemoglobin are substantially equal, such as a third wavelength comprised between 796 nm and 810 nm, and preferably equal to 810 nm;

This takes in to account the tissue absorbance of the relevant area in the estimation of the local metabolic parameter(s), the reception step comprises reception of measured light intensities for a fourth wavelength comprised between 700 nm and 800 nm, and preferably equal to 750 nm, the calculation step consisting of calculating the absorbance values from values of measured light intensities for the four wavelengths.

This improves the estimation quality of the local metabolic parameter(s), the determination step comprises resolution of a system of equations connecting a set of unknowns comprising:
concentration of oxyhemoglobin,
concentration of deoxyhemoglobin and
a tissue absorption coefficient, to the absorbance values calculated at said and at least three wavelengths as a function of molar values of absorptivity for said and at least three wavelengths;

the determination step comprises the resolution of a following system:

$$\begin{bmatrix} [HbO_2] \\ [Hb] \\ k \end{bmatrix} = l^{-1} \begin{bmatrix} \alpha_{v1,HbO_2} & \alpha_{v1,Hb} & \mu_{v1} \\ \alpha_{v2,HbO_2} & \alpha_{v2,Hb} & \mu_{v2} \\ \alpha_{v3,HbO_2} & \alpha_{v3,Hb} & \mu_{v3} \end{bmatrix}^{-1} \begin{bmatrix} A_{v1} \\ A_{v2} \\ A_{v3} \end{bmatrix}$$

With $\alpha_{v1,HbO_2}$, $\alpha_{v2,HbO_2}$, $\alpha_{v3,HbO_2}$ the molar absorptivities of the oxyhemoglobin at the three wavelengths v1, v2, v3, $\alpha_{v1,Hb}$, $\alpha_{v2,Hb}$, $\alpha_{v3,Hb}$ the molar absorptivities of the deoxyhemoglobin at the three wavelengths v1, v2, v3, $\mu_{v1}$, $\mu_{v2}$, $\mu_{v3}$ the molar absorptivities of the tissue area at the wavelengths v1, v2, v3, l the distance travelled by the light;

the determination step comprises resolution of a system of equations by a regularised optimisation method, This improves the estimation quality of the local metabolic parameter(s).

The invention also relates to a computer program product comprising a program code recorded on a data medium readable by a computer for executing the method described hereinabove when the computer program is applied to a computer to be executed.

The invention also relates to an estimation device of at least one local metabolic parameter of a tissue area of a patient, remarkable in that it comprises a processing unit programmed to perform the steps of the method described hereinabove.

PRESENTATION OF FIGURES

Figure 2:
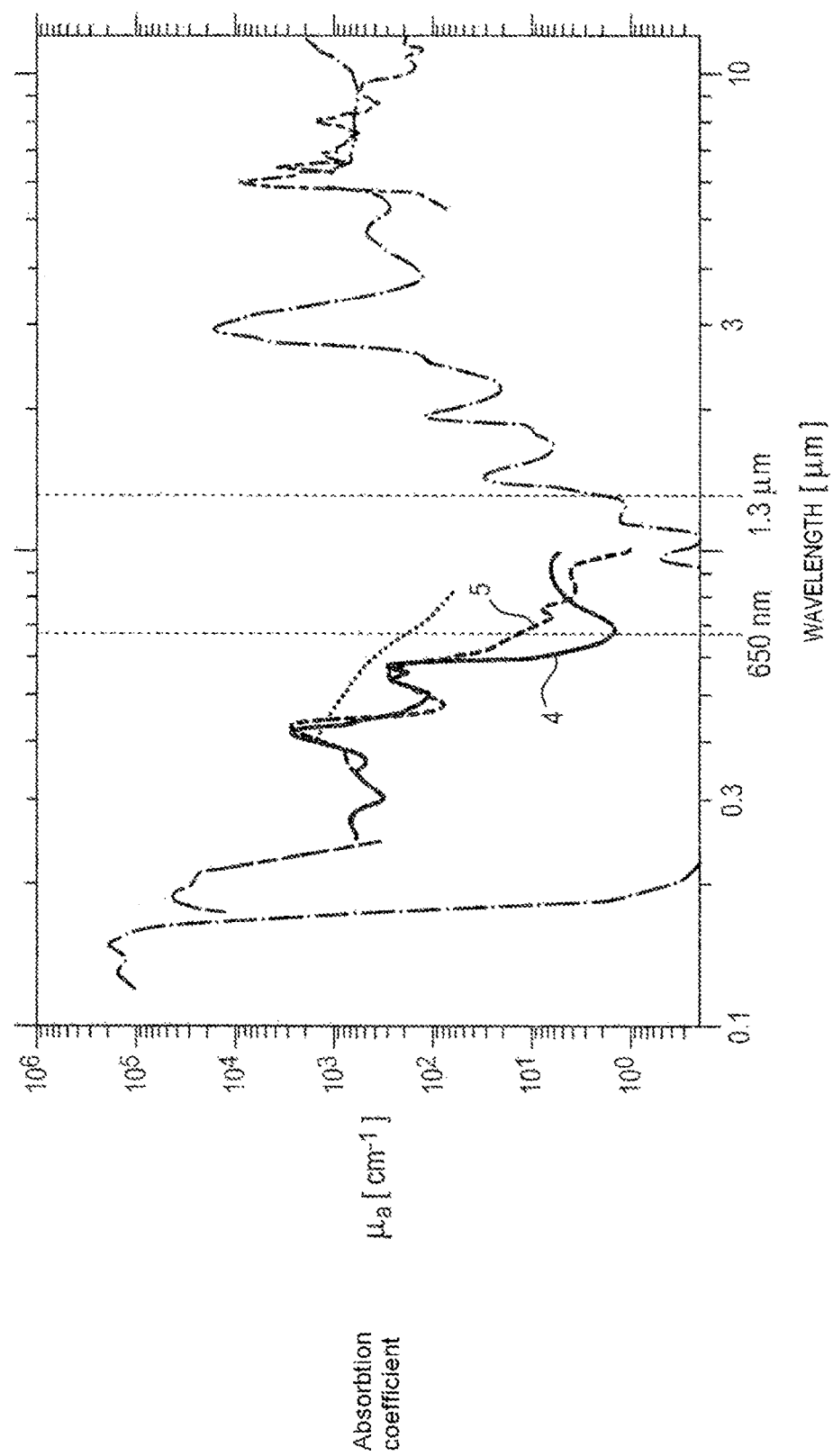
Figure 3:
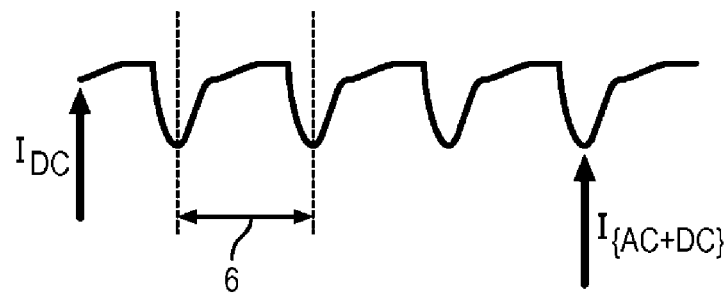
Figure 4:
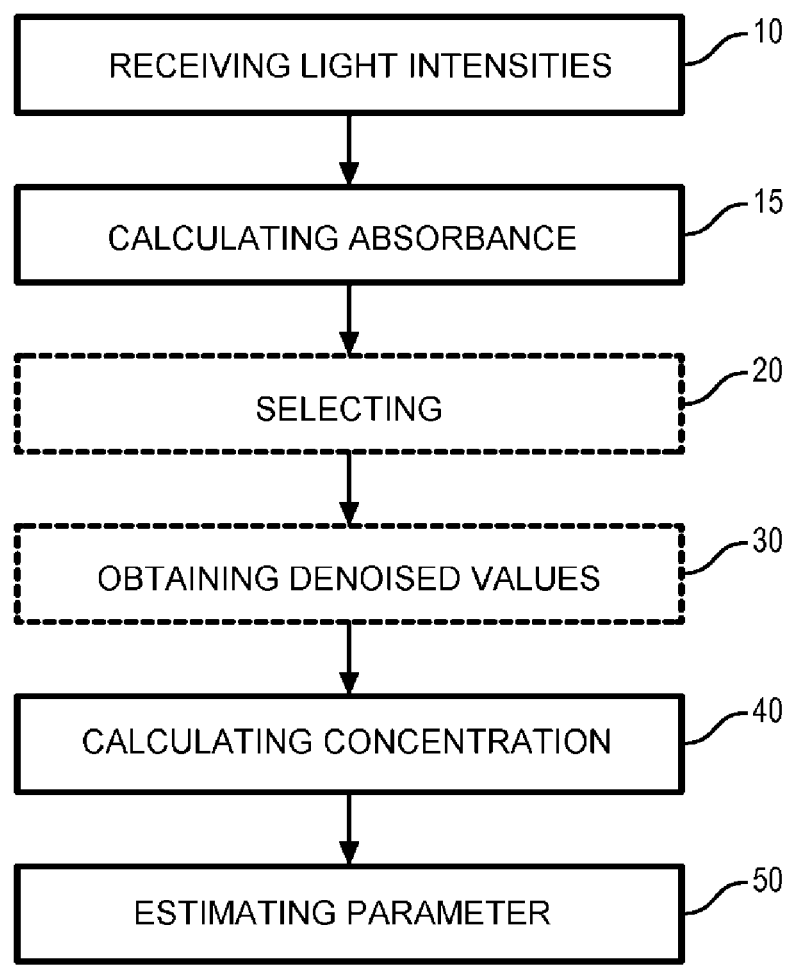
Figure 5:
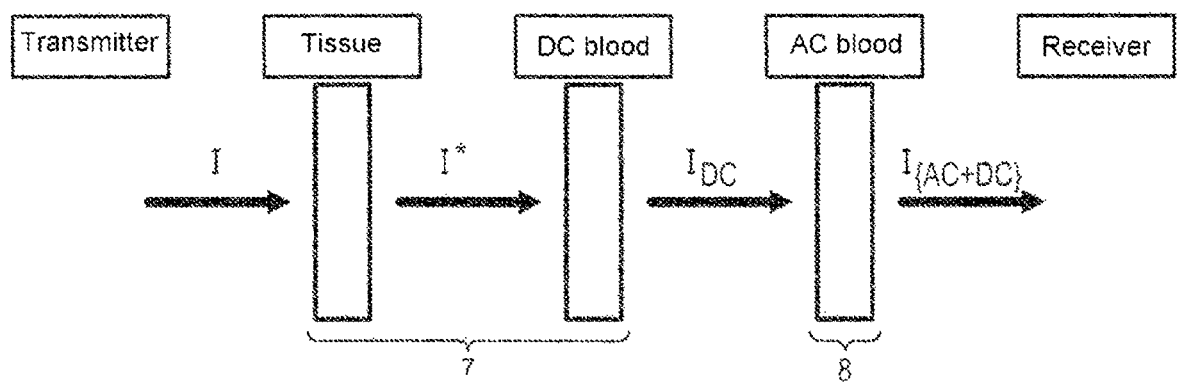
Figure 6:
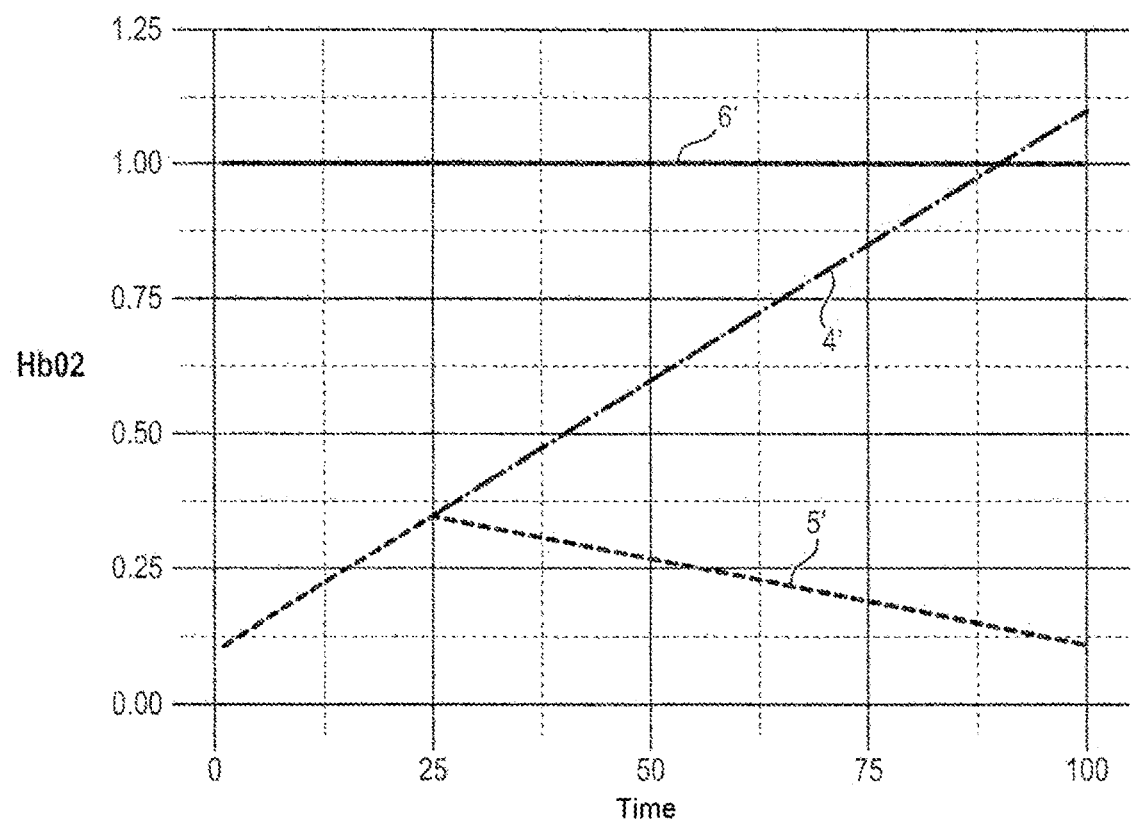
Figure 7:
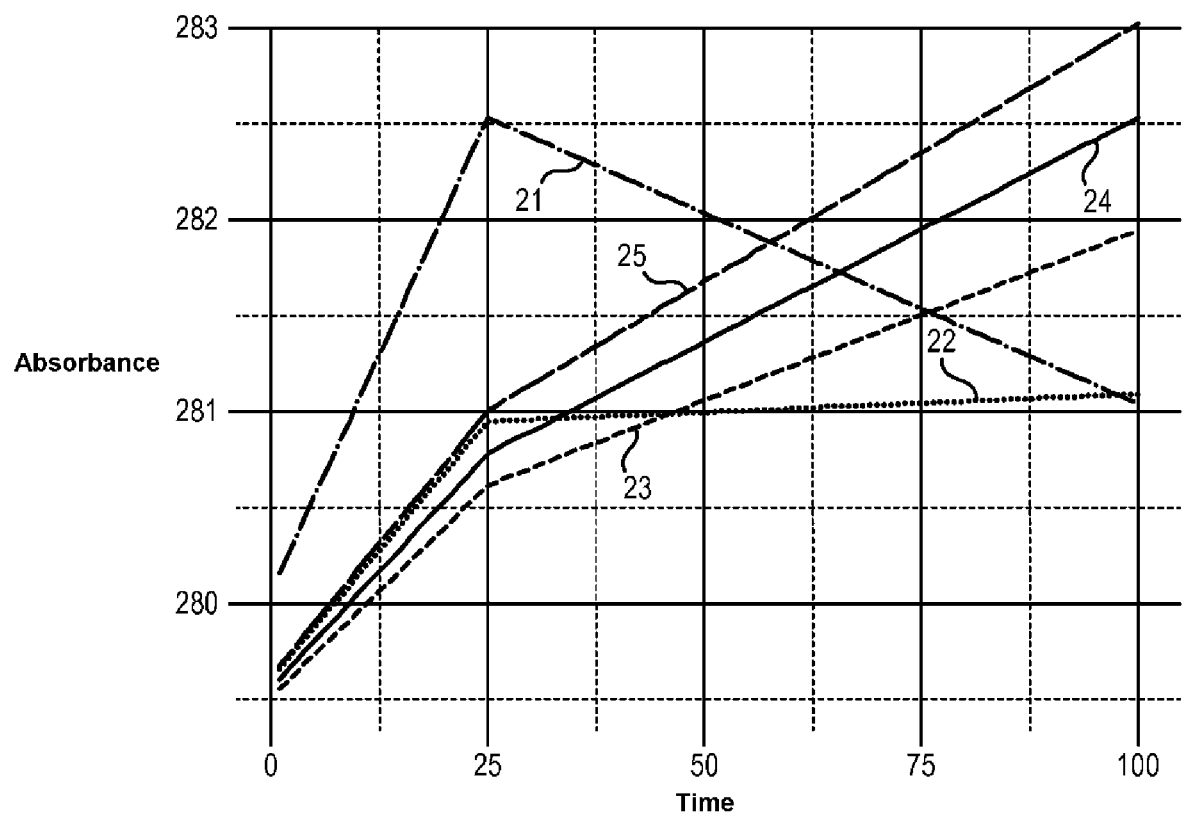
Figure 8:
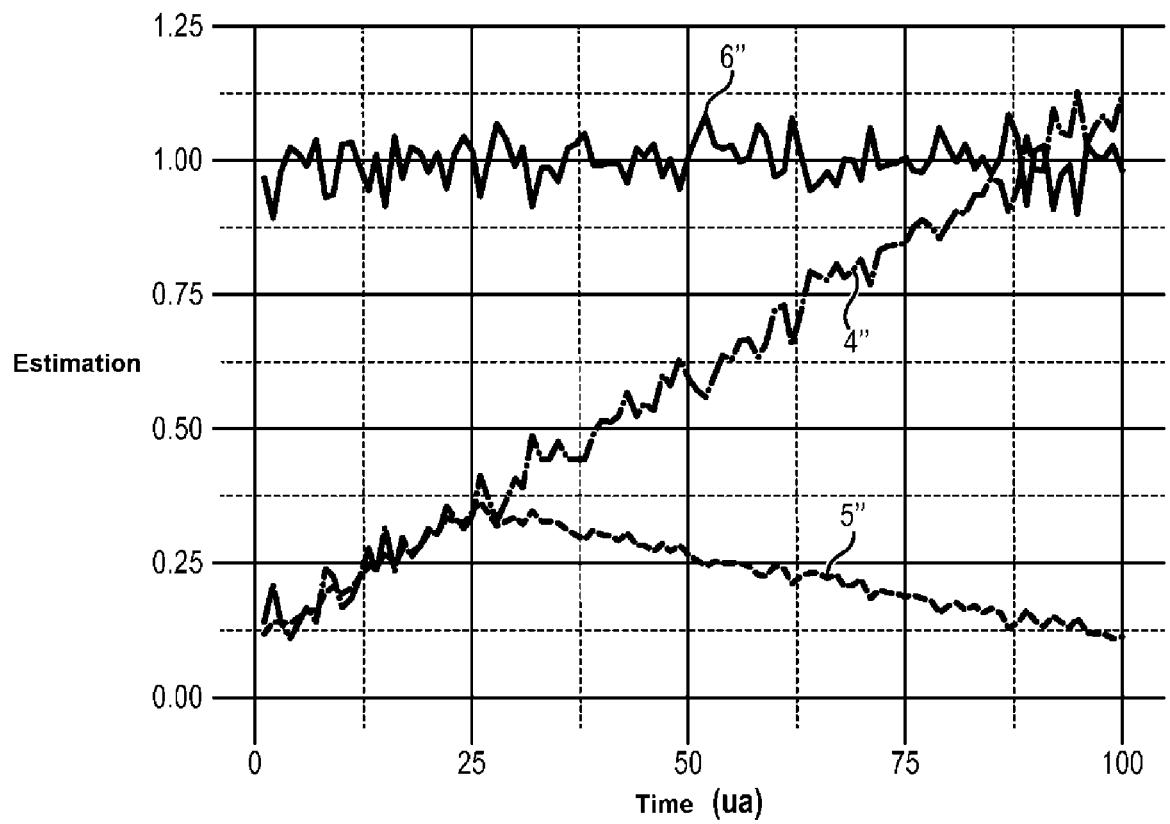

Other characteristics and advantages of the invention will emerge from the following description which is purely illustrative and non-limiting and must be considered in light of the appended drawings, in which:

FIG. 1 schematically illustrates an acquisition device for measuring light intensities at different wavelengths, FIG. 2 illustrates absorption curves of oxyhemoglobin and deoxyhemoglobin, FIG. 3 illustrates an example of a curve of measured light intensities at a given wavelength, FIG. 4 illustrates an example of a method for estimating local metabolic parameters, FIG. 5 is a functional representation of elements absorbing light, FIG. 6 illustrates the evolution as a function of time of concentrations of oxyhemoglobin and deoxyhemoglobin, as well as a tissue component, FIG. 7 illustrates simulated values of absorbance for different wavelengths, FIG. 8 illustrates the evolution as a function of time of estimated concentrations of oxyhemoglobin and deoxyhemoglobin.

DETAILED DESCRIPTION

The invention will now be described in more detail in reference to a device and a method for estimating metabolic parameters of the digestive tract in real time and non-invasively.

Of course, the present invention is not limited to estimation of metabolic parameters of the digestive tract but can be applied to other organs such as kidneys, liver, or any other organ subject to a therapeutic operation which can perturb its microcirculation.

1. ACQUISITION DEVICE 1.1. Structure of the Acquisition Device

The acquisition device is adapted to:

emit light in a tissue area of interest (i.e. for which the aim is to estimate local metabolic parameters) at at least three different wavelengths comprised between 600 and 1000 nm, and capture reflected light which has passed over the tissue area for said at least three wavelengths.

In reference to FIG. 1, this illustrates an example of an acquisition device for measuring data necessary for estimating local metabolic parameters of the digestive tract.

This device is based on measuring light intensities. This measuring is performed at the tissue for which the aim is to estimate local metabolic parameters. Such a device is especially described in document US2012/209086.

It comprises a catheter 1, a processor 2 and a memory 3 in which measuring software is stored for performing a sequence of measurements.

The catheter 1 comprises one of the plating means 11, 12 and an optical sensor at its distal end.

The plating means guarantee that the transmitter/receiver distance remains unchanged and the transmitter/receiver couple is immobile relative to the measuring area during acquisition of light signals.

In the case of hollow organs, the plating means can comprise an inflatable balloon 11 and a relatively rigid support 12 on which is mounted the optical sensor. The inflatable balloon 11 and the support 12 assure good plating of the optical sensor against the wall of the tissue when the inflatable balloon 11 is deployed. The fact that the support 12 is relatively rigid prevents deformation of the optical sensor, such deformation risking impairing modification of the arrangement of the elements constituting the optical sensor.

The optical sensor emits light in the tissue and receives light reflected by the latter. In the embodiment illustrated in FIG. 1 the optical sensor comprises three monochromatic light-emitting diodes 121, 122, 123 and a receiver 124. The receiver 124 measures the light intensity having passed through the different media of the measuring area.

Each diode 121, 122, 123 is preferably adapted to emit light radiation at a given wavelength different to the emission wavelength of the two other diodes.

Advantageously, the emission wavelengths of the three diodes 121, 122, 123 are selected as a function of the absorptivity of the different types of hemoglobin—including especially saturated hemoglobin or "oxyhemoglobin" and non-saturated hemoglobin or "deoxyhemoglobin"—present in the tissue the local metabolic parameters are to be estimated.

FIG. 2 illustrates the absorption curves of the oxyhemoglobin 4 and deoxyhemoglobin 5. As can be seen on these curves:
  the light absorption of the deoxyhemoglobin 5 is greater than the light absorption of the oxyhemoglobin 4 in a range of wavelengths comprised between 600 nm and 700 nm,
  the light absorption of the oxyhemoglobin 4 is greater than the light absorption of the deoxyhemoglobin 5 in a range of wavelengths comprised between 900 nm and 1000 nm.

Finally, light absorptions of the oxyhemoglobin 4 and deoxyhemoglobin 5 are substantially equal in a range of wavelength comprised between 750 and 850 nm.

Preferably, the three diodes 121, 122, 123 of the optical sensor are selected such that:
  the first diode 121 emits light at a first wavelength of 660 nm,
  the second diode 122 emits light at a second wavelength of 906 nm, and
  the third diode 123 emits light at a third wavelength corresponding to that of an isobestic point, that is, between 796 nm and 810 nm and preferably equal to 810 nm.

Within the scope of the present invention "isobestic point" means a wavelength (λ) at which oxyhemoglobin and deoxyhemoglobin have substantially the same absorbance.

Advantageously, the optical sensor can comprise a fourth diode (not shown) adapted to emit light radiation at a fourth wavelength comprised between 700 nm and 800 nm, and preferably equal to 750 nm.

As will be described in more hereinbelow, the presence of a fourth diode emitting at a fourth wavelength (different to the emission wavelengths of the first, second and third diodes 121, 122, 123) improves precision of the calculations made by the method described hereinbelow for estimating local metabolic parameters of the patient. Also, the fact of selecting a wavelength comprised between 700 and 800 nm for the fourth diode cancels out the majority of noise generated by the acquisition device.

Preferably, the distance between each of the diodes 121, 122, 123 of the optical sensor is less than five millimetres so that the radiation emitted by each of the diodes passes through substantially identical tissue. This ensures homogeneity of the measurements of light intensities taken at the different wavelengths.

1.2. Operating Principle of the Acquisition Device

The operating principle of the device described hereinabove is as follows.

To take a measurement the practitioner shifts the catheter 1 over the surface of an area of interest for which he wants to estimate local metabolic parameters.

Once the optical sensor is positioned at the area of interest, the practitioner controls deployment of the inflatable balloon 11, which inflates, causing plating of the optical sensor against the wall of the area of interest.

The practitioner then controls emission of light radiation by the optical sensor. Each diode 121, 122, 123 emits light at its emission wavelength. The emission of radiation by each of the diodes 121, 122, 123 is done sequentially over time, that is, the diodes 121, 122, 123 emit light one after the other. The fact that the diodes 121, 122, 123 emit no radiation simultaneously prevents any interference at the receiver 124.

The diodes 121, 122, 123 are cyclically activated at an activation frequency far greater (i.e. between 100 and 1000 times more) than the heartbeat frequency of the patient. This ensures coherence of signals recorded by the receiver 124 relative to the variation over time of the concentrations of oxyhemoglobin and deoxyhemoglobin. For example, the activation frequency is 100 Hertz.

1.3. Measuring a Plurality of Light Intensities

Each wavelength produces a plurality of measured light intensities during a period of the cardiac cycle.

Of course, light intensities can be measured (at different emission wavelengths of the diodes) over several periods of the cardiac cycle.

FIG. 3 illustrates an example of a curve of measured light intensities at a given wavelength for four periods 6 of the cardiac cycle.

The measured light intensities by means of the acquisition device described hereinabove are then used to estimate the local metabolic parameters. These local metabolic parameters can be calculated for different instants of the cardiac cycle as a function of the needs of the practitioner.

1.4. Use of Measured Light Intensities for Calculating Absorbance Values

The acquisition device measures light intensities used to estimate absorbances representative of the different media constituting the measuring area, especially venous blood, arterial blood, total blood and tissue. This will be described in more detail hereinbelow.

Venous blood corresponds to an amount of non-pulsed blood contained permanently in the tissue of the measuring area. Arterial blood corresponds to an amount of pulsed blood by the heart, contributed by the macro-circulatory arterial flow. Total blood corresponds to the presence of venous blood and arterial blood in the relevant tissue.

Absorbance corresponds to the result of a ratio between two light intensities which can be measured, known, or estimated. These absorbance values are calculated for each wavelength.

For example and in reference to FIG. 5 it is possible to calculate the following absorbances:
absorbance of the tissue $A_t$ which is equal to the ratio between:
a light intensity I* (at a given wavelength) corresponding to radiation having passed through tissue in the absence of blood; this light intensity is obtained by means of calibration which will be described hereinbelow, and
light intensity I (at the given wavelength) emitted by one of the diodes of the optical sensor; this light intensity is known,
giving:

$$A_t = -\log_{10}\left(\frac{I^*}{I}\right)$$

absorbance of venous blood $A_{DC}$ which is equal to the ratio between:
light intensity I*, and
light intensity $I_{DC}$ corresponding to light having passed through tissue and non-pulsing blood; this intensity is estimated by selection—from all the measured light intensities during a period of the cardiac cycle—of the light intensity measured for which it is supposed that the amount of pulsed blood is zero (for example by detection of maxima from all the measured light intensities as illustrated in FIG. 3), $$A_{DC} = -\log_{10}\left(\frac{I_{DC}}{I^*}\right)$$

absorbance of the arterial blood $A_{AC}$ which is equal to the ratio between:
light intensity $I_{DC}$, and
light intensity $I_{AC+DC}$ corresponding to the light having passed through tissue, non-pulsing blood and pulsed blood; this intensity is estimated by selection—from all the measured light intensities during a period of the cardiac cycle—of the light intensity measured for which it is supposed that the amount of pulsed blood is maximum (for example by detection of minima from all the measured light intensities as illustrated in FIG. 3), $$A_{AC} = -\log_{10}\left(\frac{I_{[AC+DC]}}{I_{DC}}\right)$$

The total absorbance $A_{total}$ can be characterized as the sum of the above three absorbances:

$$A_{total} = -\log\left(\frac{I_{[AC+DC]}}{I}\right)$$
$$= -\log\left(\frac{I_{[AC+DC]}}{I_{DC}} \frac{I_{DC}}{I^*} \frac{I^*}{I}\right)$$
$$= -\log\left(\frac{I_{[AC+DC]}}{I_{DC}}\right) - \log\left(\frac{I_{DC}}{I^*}\right) - \log\left(\frac{I^*}{I}\right)$$
$$= A_{AC} + A_{DC} + A_t$$

2. ESTIMATION OF LOCAL METABOLIC PARAMETERS

A method for estimating local metabolic parameters will now be described in reference to the digestive tract.
As illustrated in FIG. 4, the method comprises the steps consisting of:
receiving 10 of measured light intensities by the acquisition device for three different wavelengths (or more),
calculating 15 absorbance values from measured light intensities,
determining 40 concentrations of oxyhemoglobin and deoxyhemoglobin,
estimating 50 one (or more) metabolic parameter(s).
In reference to FIG. 5, the measured light intensities are a function of a static component 7 and a dynamic component 8. The static component 7 is representative of the light absorptivity of relevant tissue as an amount of non-pulsed blood (i.e. venous blood). The dynamic component 8 represents as such the light absorptivity of pulsed blood (i.e. arterial blood). Each of these categories of blood (venous blood, arterial blood) comprises oxyhemoglobin and deoxyhemoglobin in different proportions.
The invention considers the light absorptivity of tissue by the use of a third wavelength corresponding to the isobestic point.
The local metabolic parameters likely to be calculated comprise:
concentrations of oxyhemoglobin ($HbO_2$) and deoxyhemoglobin (Hb), and therefore a rate of oxygenation,
a contribution of oxygen,
oxygen consumption,
a perfusion index, etc.
Estimation of these parameters is done by using absorbance values of the digestive tract obtained from measured light intensities for at least three wavelengths by the acquisition device described hereinabove, these wavelengths being selected as a function of the light absorptivity of different types of hemoglobin, and especially oxyhemoglobin $HbO_2$ and deoxyhemoglobin Hb.

2.1. Calculation of Concentrations of Oxyhemoglobin $HBO_2$ and Deoxyhemoqlobin Hb
Below, it is supposed that absorbance values of the digestive tract were obtained from measured light intensities by the acquisition device for the three following wavelengths:
a first length equal to 660 nm at which deoxyhemoglobin Hb absorbs more light beams (than oxyhemoglobin),
a second wavelength equal to 905 nm at which oxyhemoglobin $HbO_2$ absorbs more light beams (than deoxyhemoglobin), and
a third wavelength equal to 810 nm at which light absorptions of oxyhemoglobin $HbO_2$ and of deoxyhemoglobin Hb are substantially equal.
Use of the third wavelength equal to 810 nm omits the tissue component. In fact for each wavelength v applying the Beer-Lambert law gives:

$$A_v = l(\alpha_{v,1}[1] + \alpha_{v,2}[2] + \alpha_{v,3}[3] + \mu_v k)$$

With:
$A_v$ absorbance at the wavelength v,
l distance traveled by the light,
$\alpha_{v,1}$ molar absorptivity of the type 1 at the wavelength v,
$\alpha_{v,2}$ molar absorptivity of the type 2 at the wavelength v,
$\alpha_{v,3}$ molar absorptivity of the type 3 at the wavelength v,
[1] concentration of the type 1,
[2] concentration of the type 2,

[3] concentration of the type 3, $\mu_\nu$ tissue absorption coefficient, k a cushioning parameter for adjusting tissue absorptivity.

According to the Beer-Lambert law, absorbance of a solution is proportional to the concentration of substances in solution, on condition of being placed at the wavelength at which the substance absorbs light beams. This is why the wavelength is selected as a function of the substance whereof the concentration is to be known. In the case in point, the three wavelengths are selected as a function of the absorptivity of hemoglobin in its different states (saturated/non-saturated).

The application of this equation for each of the three wavelengths provides a system of three equations with four unknowns ([1], [2], [3] and k).

The choice of a wavelength of 810 nm (isobestic point) simplifies this relation since one of the types (type 3) comprises the two others (type 1 and 2). More precisely, type 3 which corresponds to total hemoglobin tHb consists of oxyhemoglobin $HbO_2$ and deoxyhemoglobin Hb.

The concentration of total hemoglobin [tHb] can therefore be defined by:

$$[HbO_2]+[Hb]=[tHb].$$

Supposing the tissue absorption coefficient $\mu_\nu$ constant for all relevant wavelengths, the following equation system results:

$$A_{660}=l(\alpha_{660,HbO_2}[HbO_2]+\alpha_{660,Hb}[Hb]+\mu_{660}k)$$

$$A_{810}=l(\alpha_{810,HbO_2}[HbO_2]+\alpha_{810,Hb}[Hb]+\mu_{810}k)$$

$$A_{905}=l(\alpha_{905,HbO_2}[HbO_2]+\alpha_{905,Hb}[Hb]+\mu_{905}k)$$

The following matricial form is obtained:

$$\begin{bmatrix} [HbO_2] \\ [Hb] \\ k \end{bmatrix} = l^{-1}M^{-1} \begin{bmatrix} A_{660} \\ A_{810} \\ A_{905} \end{bmatrix}$$

$$\text{With } M = \begin{bmatrix} \alpha_{660,HbO_2} & \alpha_{660,Hb} & \mu_{660} \\ \alpha_{810,HbO_2} & \alpha_{810,Hb} & \mu_{810} \\ \alpha_{905,HbO_2} & \alpha_{905,Hb} & \mu_{905} \end{bmatrix}$$

All the magnitudes of the matrix M—specifically the different values of molar absorptivity—are constants which are obtained experimentally or by the literature. The absorbance values of the matrix $$\begin{bmatrix} A_{660} \\ A_{810} \\ A_{905} \end{bmatrix}$$

are as such calculated from measured light intensities by means of the acquisition device described hereinabove. Finally, the distance l travelled by light is also known and is a function of the distance between each diode 121, 122, 123 and the receiver 124 (each distance diode/receiver being known).

By way of indication, the table hereinbelow (data by W. B. Gratzer, Med. Res. Council Labs, Holly Hill, London and N. Kollias, Wellman Laboratories, Harvard Medical School, Boston) provides the values of molar absorptivity (in $cm^{-1}$/M) of oxyhemoglobin and deoxyhemoglobin for different wavelengths:

| nm | HbO2 | Hb |
| --- | --- | --- |
| 660 | 319 | 3226 |
| 750 | 518 | 1405 |
| 810 | 864 | 718 |
| 850 | 1058 | 691 |
| 906 | 1209 | 770 |

The value of the tissue absorption coefficient $\mu_\nu$ can also be obtained experimentally or by the literature and depends on the relevant tissue (digestive tract, liver, rate, heart, etc.). For example in the case of the digestive tract, the value of the tissue absorption coefficient $\mu_\nu$ can be relevant as equal to 1000 $cm^{-1}$ for each of the different wavelengths.

Concentrations of oxyhemoglobin [$HbO_2$] and deoxyhemoglobin [Hb] can therefore be calculated.

Advantageously, these concentrations can be calculated for different categories of blood (i.e. venous blood, arterial blood or total blood) from absorbances of venous blood $A_{DC}$, absorbances of arterial blood $A_{DC+AC}$, or of total blood at different wavelengths. For example, the concentration of oxyhemoglobin in arterial blood can be calculated from the difference in concentration of oxyhemoglobin between total blood and venous blood. Absorbance measurements are preferably taken over a measuring time sufficiently short for their value to be substantially constant during a heartbeat.

Resolution of this system can be done by direct resolution of the equation system (3 equations/3 unknowns). This limits the material resources necessary for estimating concentrations of oxyhemoglobin [$HbO_2$] and deoxyhemoglobin [Hb].

Yet, a disadvantage of direct resolution is that it is sensitive to noise, which makes measuring unstable and can misstate the problem (i.e. without solution or infinite solutions).

A solution for rectifying this drawback consists of resolving this system by a regularised optimisation method for preferring a particular solution marked by properties which seem pertinent. Such a method can be the method of least squares regularised by using a regularisation term for preferring a particular solution marked by properties which seem pertinent. Advantageously this regularisation term is selected as a standard 2 to avoid parsimony in the solution.

2.2. Calculation on a Set of Absorbance Values

Advantageously, estimation of concentrations of oxyhemoglobin [$HbO_2$] and deoxyhemoglobin [Hb] can be made on sets of absorbance values calculated at each of the three wavelengths. This improves estimation precision by limiting influence of the measuring noise in calculating concentrations of oxyhemoglobin [$HbO_2$] and deoxyhemoglobin [Hb].

More precisely, instead of calculating concentrations of oxyhemoglobin [$HbO_2$] and deoxyhemoglobin [Hb] from a triplet of absorbance values ($A_{660}$, $A_{810}$ $A_{905}$) for the three wavelengths, concentrations of oxyhemoglobin [$HbO_2$] and deoxyhemoglobin [Hb] are estimated from a triplet of "denoised" values ($f(Ak_{660},n), f(Ak_{810},n), f(Ak_{905},n)$) for the three wavelengths, each "denoised" value corresponding to the result of the treatment of a plurality (two, three, four, ten or more) of absorbance values for the relevant wavelength by a linear or non-linear function $f$ With:

$Ak_\nu$ a "k-th" absorbance value at the wavelength v, n, the number of relevant absorbance values.

The linear or non-linear function can be:

a median filter (non-linear function), a sliding average, or any type of function known to those skilled in the art for minimising the impact of the measuring noise from a set of absorbance values.

In this case, the method comprises a determination step of "denoised" values at each of the three wavelengths (step 30 of FIG. 2).

Of course, use of a triplet of "denoised" values supposes that concentrations of oxyhemoglobin [HbO$_2$] and deoxyhemoglobin [Hb] vary slowly relative to the sampling frequency. This is why at a sampling frequency of 100 Hz, n=5 will preferably be chosen.

2.3. Calibrating

In some variant embodiments, the method can comprise a calibrating step.

Calibrating evaluates the amount of light absorbed by tissue in the absence of blood. Calibrating is possible since the mucous of the digestive tract is homogeneous in part.

The acquisition device is placed at a tissue area of interest to carry out this calibrating. Next, blood is exsanguinated in the area of interest, optionally by introducing physiological serum to this area to replace blood.

As a function of local metabolic parameters to be estimated, the light intensity having passed through tissue is measured:

for a given wavelength, such as a wavelength equal to 810 nm, or for all wavelengths (660 nm, 810 nm, 905 nm) as a function of the nature of the tissue analysed and the characteristics of the acquisition device.

In all cases, the intensity measured $I_{exsanguinated}$ (at each wavelength) is representative of the amount of light absorbed by tissue l* only since the latter contains more blood in the measuring area.

This calibration calculates the absorbances for each wavelength:

of venous blood:

$$A_{DC}\left(A_{DC} = -\log_{10}\left(\frac{I_{DC}}{I^*}\right)\right),$$

of arterial blood, and of total blood $A_{total}$.

From these different absorbance categories, the concentrations of oxyhemoglobin and deoxyhemoglobin can be calculated:

for venous blood, arterial blood, and total blood in the same way as previously but without the 3$^{rd}$ cushioning parameter since contribution of the tissue is no longer present.

2.4. Calculation of Other Local Metabolic Parameters

From estimated concentrations of oxyhemoglobin [HbO2] and deoxyhemoglobin [Hb], many local metabolic parameters can be calculated, such as a rate of oxygenation of the tissue area.

2.4.1. Rate of Oxygenation: First Calculation Method

Estimation of the rate of oxygenation of venous, arterial or total blood SxO$_2$ can be obtained by applying the following formula:

$$SxO_2 = \frac{[HbO_2]_x}{[HbO_2]_x + [Hb]_x}.$$

With:

SxO$_2$, the rate of oxygenation of the blood "x",

[HbO$_2$]$_x$ the concentration of oxyhemoglobin of the blood "x", and

[Hb]$_x$ the concentration of deoxyhemoglobin of the blood "x", and where the letter "x" designates either venous, arterial or total blood.

This method uses resolution of the system involving the cushioning parameter k. By way of observation, concentration of oxyhemoglobin or deoxyhemoglobin of total blood can be obtained respectively by the sum of concentrations of oxyhemoglobin or deoxyhemoglobin of venous blood and of arterial blood.

It should be noted that the rate of oxygenation of the tissue area is equivalent to the rate of oxygenation of total blood.

2.4.2. Rate of Oxygenation: Second Calculation Method

Calculation of this rate of oxygenation can also be obtained by direct estimation of the concentration of total hemoglobin after the previously described calibrating step. This omits the cushioning parameter k.

2.4.3. Calculation of Oxygen Contribution

It is also possible to calculate the contribution of oxygen from the concentration of oxyhemoglobin [HbO$_2$] linked to arterial blood, that is, by using the absorbance of the dynamic component 8 of FIG. 5.

The contribution of oxygen is obtained by multiplying the concentration of oxyhemoglobin by the Hüfner constant.

Here too, estimation of this concentration can be done by using a concentration of total hemoglobin estimated from absorbance at 810 nm after calibrating of the acquisition device (such as described in point 2.3).

2.4.4. Calculation of Oxygen Consumption

Oxygen consumption is estimated from concentrations of oxyhemoglobin of arterial blood and venous blood, respectively calculated from absorbances of arterial blood and venous blood. For this, it can be useful to estimate the absorbance of the static blood component and estimate the component of dynamic blood by the respective use of calibration and selection of instant of adequate measurement during the cardiac cycle (see for example FIGS. 3 and 4). For each of these absorptions, one of the methods described hereinabove can be applied to obtain concentrations of saturated hemoglobin and non-saturated hemoglobin.

According to an alternative, oxygen consumption can be estimated from concentrations of oxyhemoglobin of total blood and of venous blood. The concentrations of oxyhemoglobin of arterial blood can be obtained by subtracting the concentrations of oxyhemoglobin of venous blood from total blood.

The calibration phase can be used to differentiate the static component from the tissue component.

2.5. Use of a Fourth Wavelength for Estimating Local Metabolic Parameters

As indicated previously in reference to the acquisition device illustrated in FIG. 1, measurement of light intensity at a fourth wavelength can be used to calculate the local metabolic parameters of the patient.

Use of this fourth wavelength improves estimation precision of local calculated parameters.

The choice of the value of this additional wavelength is guided by several factors:

the wavelength of the isobestic point is a direct reflection of the total hemoglobin volume. In this, it proposes an interesting alternative to be provided to the practitioner in case of noised measurement for the first, second and third wavelengths, it is known that measuring in the visible field is more subject to measuring noise than measuring in infrared; it is therefore preferable to favour measuring near infrared, study of the presentation of the system shows that a fourth wavelength near red or near the isobestic point offers greater robustness to the measuring noise during estimation of concentrations.

The presentation places a limit on the relative error committed on the solution when the parameters of the system are modified. In this case, since the data of the problem are measured light intensities they are necessarily subject to noise and therefore tainted by error.

The table hereinbelow gives the presentation of the system for several choices of wavelengths:

| nm | Presentation |
|---|---|
| (660, 750, 906) | 44 |
| (660, 810, 906) | 50 |
| (660, 850, 906) | 126 |

In light of the table hereinabove a fourth wavelength comprised between 700 and 800 nm, and preferably equal to 750 nm will preferably be chosen. In fact, the use of a fourth wavelength equal to 750 nm minimises the presentation factor.

2.6. Example of System Resolution on Simulated Data

An example of results obtained will now be presented by executing the method described above. For this simulation, a travel length of 1.2 cm is chosen between each diode 121, 122, 123 and the receiver 124 of the optical sensor.

The extinction coefficients are those givens in the following table of molar absorptivities:

| nm | Hb02 | Hb |
|---|---|---|
| 660 | 319 | 3226 |
| 750 | 518 | 1405 |
| 810 | 864 | 718 |
| 850 | 1058 | 691 |
| 906 | 1209 | 770 |

FIG. 6 presents evolution, as a function of time:
of concentrations of oxyhemoglobin 4' and deoxyhemoglobin 5', and
of the tissue component 6'.

FIG. 7 illustrates simulated absorbance values for the following wavelengths:
660 nm (reference 21),
750 nm (reference 22),
810 nm (reference 23),
850 nm (reference 24),
906 nm (reference 25).

These simulated absorbance values are obtained by application of the Beer-Lambert law.

To evaluate the quality of estimation of concentrations, a noise is introduced to the extent where light intensity reflected. This measuring noise corresponds to a standard deviation white noise equal to 5% of the light intensity received by the receiver of the optical sensor.

Using the method described hereinabove, estimations of concentrations of oxyhemoglobin 4" and deoxyhemoglobin 5" as well as the tissue component 6" are obtained, such as illustrated in FIG. 8.

Replication over one hundred individuals produces the RMS value of the error for different choice of wavelengths. The RMS error of simulations is presented in the table hereinbelow.

| Wavelengths | HbO2 | Hb | Tissue |
|---|---|---|---|
| (660, 750, 906) | 0.030 | 0.009 | 0.039 |
| (660, 810, 906) | 0.021 | 0.007 | 0.028 |
| (660, 850, 906) | 0.062 | 0.020 | 0.086 |
| (660, 750, 810, 906) | 0.020 | 0.007 | 0.024 |

The first three lines of the previous table agree with the presentation table described earlier and shows that it is preferable to consider the frequency triplets (660, 750, 906) and (660, 810, 906).

The use of an additional wavelength (using the method of ordinary least squares to resolve the system) completes the last line of the previous table. The RMS values obtained for this last line confirms that the use of four wavelengths can contribute to interesting redundancy in estimating concentrations of oxyhemoglobin and deoxyhemoglobin.

3. CONCLUSIONS

The method described previously estimates concentrations of oxyhemoglobin and deoxyhemoglobin.

From these estimated concentrations, it is possible to calculate different metabolic parameters such as:
a rate of oxygenation from concentrations of saturated hemoglobin and non-saturated hemoglobin,
a perfusion index,
oxygen contribution,
oxygen consumption, etc.

As indicated previously, the acquisition device activates the diodes 121, 122, 123 successively and cyclically, the activation frequency of the diodes being far greater than the heartbeat frequency of the patient. When the acquisition device measures light intensities on a plurality of cardiac cycles the method according to the invention receives a set of measured light intensities on a plurality of cardiac cycles for each wavelength.

As a function of the metabolic parameter(s) to be estimated, a selection step (step 20) of light intensities for an instant of interest or instants of interest of a period of the cardiac cycle can be performed. From this selection it is possible to calculate the concentrations of oxyhemoglobin and deoxyhemoglobin for venous blood, arterial blood, and for total blood.

The selection of light intensities can be done manually, or automatically. In this case, automatic selection can be obtained by executing a detection algorithm of minima and/or maxima (and/or other points of interest) in the curves of measured light intensities at the different wavelengths, and whereof an example is illustrated in FIG. 3.

Advantageously, the method described hereinabove can be implemented in the form of program code to be run on a computer comprising a processor (configured to perform the steps of the method described hereinabove).

The values of the calculated local metabolic parameters can then be displayed on display means such as a computer screen to let the practitioner set up a diagnosis, and/or to guide him in the choice of treatment adapted to the patient.

The reader will have understood that many modifications can be made to the device and method described previously without departing materially from the new ideas described hereinabove and defined in the appended claims.

For example, in the preceding description, absorbance of arterial blood was defined as a function of the ratio between:
- minimum light intensity over a period of the cardiac cycle, and
- maximum light intensity over the same period of the cardiac cycle.

The reader will have understood that light intensity other than minimum light intensity can be selected to calculate absorbance of arterial blood at any point of the cardiac cycle.

The reader will have also understood that the blood of a patient comprises not only oxyhemoglobin and deoxyhemoglobin. Yet, within the scope of the present invention the other elements contained therein are not taken into account in the model previously described, as their impact on the quality of the tissue oxygenation of a patient is negligibly relevant.

The invention claimed is:

1. A method for estimation of at least one local metabolic parameter of a relevant tissue area of a patient, wherein the method comprises the following steps:
    shifting a catheter over a surface of the relevant tissue area, an optical sensor of an acquisition device being disposed at a distal end of the catheter,
    wherein said optical sensor is comprised of at least three diodes and a receiver, each diode emitting a light radiation at a defined wavelength different of the others diodes so that the optical sensor emits a light intensity for at least three different wavelengths comprised between 600 and 1000 nm, the at least three different wavelengths being selected as a function of absorptivity of oxyhemoglobin and deoxyhemoglobin, said receiver measuring light intensity for the at least three different wavelengths,
    positioning said optical sensor, against the wall of the relevant tissue area,
    emitting each light radiation by each diode of the optical sensor at each of the at least three different wavelengths,
    receiving said light intensity having passed through the relevant tissue area, said light intensity being measured by the receiver for the at least three different wavelengths so as to determine received light intensities,
    wherein the step of receiving said light intensity comprises a step of: receiving, a plurality of measured light intensities at different instants of a cardiac cycle for each of the at least three different wavelengths,
    generating curves of said received light intensities over several cardiac cycles,
    selecting at least one instant of the cardiac cycle of each plurality of measured light intensities so as to determine each selected light intensity for each wavelength,
    calculating absorbance values from each selected light intensity for the at least three different three wavelengths,
    determining a concentration of oxyhemoglobin and a concentration of deoxyhemoglobin from the absorbance values calculated for the at least three different three wavelengths, and
    estimating at least one local metabolic parameter of the relevant tissue area of the patient from said concentrations of oxyhemoglobin and said concentration of deoxyhemoglobin,
    wherein the step of estimating comprises: estimating oxygen consumption in the relevant tissue area from said concentrations of oxyhemoglobin and said concentration of deoxyhemoglobin in the total blood and in the venous blood,
    wherein the step of selecting comprises: detecting at least one of a maxima and a minima in the curves of said received light intensities at the at least three wavelengths,
    wherein, from all the measured light intensities of each wavelength, a light intensity for which an amount of arterial blood is minimum in the relevant tissue area such that the determined concentrations are representative of concentration of oxyhemoglobin and deoxyhemoglobin in the venous blood, and
    wherein, from all the measured light intensities, light intensities for which the amount of arterial blood is maximum in the relevant tissue area such that the determined concentrations are representative of concentration of oxyhemoglobin and deoxyhemoglobin in the total blood.

2. The method according to claim 1, wherein the the step of estimating oxygen consumption comprises the step of estimating a rate of oxygenation of the relevant tissue area from said concentration of oxyhemoglobin and said concentration of deoxyhemoglobin.

3. The method according to claim 1, which further comprises an additional step of obtaining denoised values corresponding to the results of a mathematical function applied to a plurality of absorbance values for each of at least the three wavelengths, the determination step consisting of calculating the concentrations of oxyhemoglobin and deoxyhemoglobin from the denoised values, wherein the step of obtaining denoised value occurring between the selection step and the determination step.

4. The method according to claim 1, wherein the reception step comprises the reception of measured light intensities for:
    a first wavelength at which the light absorption of deoxyhemoglobin is greater than the light absorption of oxyhemoglobin,
    a second wavelength at which the light absorption of oxyhemoglobin is greater than the light absorption of deoxyhemoglobin, and
    a third wavelength corresponding to an isobestic point at which the light absorptions of oxyhemoglobin and of deoxyhemoglobin are equal.

5. The method according to claim 4, wherein the first wavelength is comprised between 600 and 700 nm.

6. The method according to claim 5, wherein the first wavelength is equal to 660 nm.

7. The method according to claim 4, wherein the second wavelength is comprised between 900 and 1000 nm.

8. The method according to claim 7, wherein, wherein the second wavelength is equal to 906 nm.

9. The method according to claim 4, wherein the third wavelength is comprised between 796 nm and 810 nm.

10. The method according to claim 9, wherein the third wavelength is equal to 810 nm.

11. The method according to claim 1, wherein the reception step comprises the reception of measured light intensities for a fourth wavelength comprised between 700 nm and 800 nm, the calculation step consisting of calculating the absorbance values from values of measured light intensities for the four wavelengths.

12. The method according to claim 11, wherein the fourth wavelength is equal to 750 nm.

13. The method according to claim 1, wherein the determination step comprises resolution of a system of equations linking a set of unknowns comprising:
the concentration of oxyhemoglobin,
the concentration of deoxyhemoglobin, and
a tissue absorption coefficient,
said equations using absorbance values as a function of molar absorptivity values in accordance with the Beer-Lambert law using at least three wavelengths.

14. The method according to claim 13, wherein the determination step comprises resolution of a following system:

$$\begin{bmatrix} [HbO_2] \\ [Hb] \\ k \end{bmatrix} = l^{-1} \begin{bmatrix} \alpha_{v1,HbO_2} & \alpha_{v1,Hb} & \mu_{v1} \\ \alpha_{v2,HbO_2} & \alpha_{v2,Hb} & \mu_{v2} \\ \alpha_{v3,HbO_2} & \alpha_{v3,Hb} & \mu_{v3} \end{bmatrix}^{-1} \begin{bmatrix} A_{v1} \\ A_{v2} \\ A_{v3} \end{bmatrix}$$

With
k a tissue absorption coefficient,
l the distance traveled by the light,
$\alpha_{v1,HbO_2}$, $\alpha_{v2,HbO_2}$, $\alpha_{v3,HbO_2}$ molar absorptivities of the oxyhemoglobin at the three wavelengths v1, v2, v3,
$\alpha_{v1,Hb}$, $\alpha_{v2,Hb}$, $\alpha_{v3,Hb}$ molar absorptivities of the deoxyhemoglobin at the three wavelengths v1, v2, v3,
$\mu_{v1}$, $\mu_{v2}$, $\mu_{v3}$ molar absorptivities of the tissue area at the wavelengths v1, v2, v3,
$A_{v1}$, $A_{v2}$, $A_{v3}$, absorbance at the wavelengths, v1, v2, v3.

15. The method according to claim 1, wherein the determination step comprises resolution of a system of equations by a regularised optimisation method.

* * * * *